(12) United States Patent
Zhong et al.

(10) Patent No.: US 7,906,314 B2
(45) Date of Patent: Mar. 15, 2011

(54) METHOD FOR THE REMOVAL OF MONOSACCHARIDE IN OLIGOSACCHARIDES PRODUCTION

(75) Inventors: Zhensheng Zhong, Guangzhou (CN); Jianhua Zhu, Edmonton (CA); XiaoLin Li, Guangzhou (CN); Xiao Yan Xu, Guangzhou (CN); Xiaomei Mu, Guangzhou (CN)

(73) Assignee: Advance Will Technology Limited, Road Town (VG)

( * ) Notice: Subject to any disclaimer, the term of this patent is extended or adjusted under 35 U.S.C. 154(b) by 0 days.

(21) Appl. No.: 11/035,685

(22) Filed: Jan. 14, 2005

(65) Prior Publication Data

US 2005/0181486 A1  Aug. 18, 2005

(30) Foreign Application Priority Data

Jan. 15, 2004 (CN) .......................... 2004 1 0015133

(51) Int. Cl.
*C07H 1/00* (2006.01)
*C12N 1/00* (2006.01)

(52) U.S. Cl. .................................. 435/255.1; 536/1.11

(58) Field of Classification Search .................. None
See application file for complete search history.

(56) References Cited

U.S. PATENT DOCUMENTS

| | | | | |
|---|---|---|---|---|
| 3,966,554 | A | * | 6/1976 | Vass et al. ............... 435/255.7 |
| 4,071,407 | A | * | 1/1978 | Hall ............................ 435/15 |
| 4,081,326 | A | | 3/1978 | Hall |
| 4,603,110 | A | | 7/1986 | Morehouse et al. |
| 5,180,669 | A | | 1/1993 | Antrim |
| 5,364,936 | A | * | 11/1994 | Oguma et al. .............. 536/103 |
| 5,652,127 | A | | 7/1997 | Mitchinson et al. |
| 5,736,533 | A | | 4/1998 | Simon et al. |
| 5,756,714 | A | | 5/1998 | Antrim et al. |
| 6,129,788 | A | * | 10/2000 | Liaw et al. ..................... 127/40 |
| 6,652,901 | B2 | | 11/2003 | Ishii |

FOREIGN PATENT DOCUMENTS

| | | |
|---|---|---|
| CA | 1 208 586 | 7/1986 |
| CA | 2 109 368 | 1/2001 |
| CN | 1288954 | 3/2001 |
| CN | 1317492 | 10/2001 |
| EP | 0 252 730 | 1/1988 |
| WO | WO 93/09244 | 5/1993 |
| WO | WO 00/12746 | 3/2000 |

OTHER PUBLICATIONS

Nakakuki, Teruo, 'Present status and future of functional oligosaccharide development in Japan', Pure Appl. Chem. vol. 74, No. 7, 1245-1251, as early as 2002.

Cheng, C. C., et al., "Production of high-content galacto-oligosaccharide by enzyme catalysis and fermentation with *Kluyveromyces marxianus*," Biotechnology Letters 28(11):793-797, Jun. 10, 2006.

Pan, Y.C., and Lee, W.C., "Production of high-purity isomaltooligosaccharides syrup by the enzymatic conversion of transflucosidase and fementation of yeast cells," Biotechnology and Bioengineering 89(7):797-804, Mar. 30, 2005.

Tieking, M., et al., "Evidence for Formation of Heterooligosaccharides by *Lactobacillus sanfranciscensis* during Growth in Wheat Sourdough," Journal of Agricultural and Food Chemistry, 53(7):2456-2461, Feb. 26, 2005.

* cited by examiner

*Primary Examiner* — Deborah K. Ware
(74) *Attorney, Agent, or Firm* — Christensen O'Connor Johnson Kindness PLLC

(57) ABSTRACT

A method for removal of the monosaccharide in oligosaccharides production which includes the step of culturing the yeast. A further step involves mixing 8%-12% (W/W) of yeast based on the weight of oligosaccharides and 0.1%-0.5% (W/W) of carbamide as nitrogen source with raw oligosaccharide syrup, and then adjusting the pH value to 4.5-6.0. A further step involves culturing the above oligosaccharides syrup at 23° C.-26° C. for 20-30 hours with intermittent agitation.

4 Claims, No Drawings

METHOD FOR THE REMOVAL OF MONOSACCHARIDE IN OLIGOSACCHARIDES PRODUCTION

FIELD OF THE INVENTION

The present invention relates to a method for the removal of monosaccharide in oligosaccharides production. The method is used to remove monosaccharide from oligosaccharides by yeast fermentation reaction.

BACKGROUND OF THE INVENTION

The oligosaccharides are a new generation of functional food or health food ingredient with special physiological effects which can promote the proliferation of colonic Liacteria of genus *Bifidobacterium* to balance the microbial ecology of the microflora in gastrointestinal tract of human being, suppress the growth of undesirable bacteria and function as an anti-dental caries. Oligosaccharides are a type of sweetener that is not absorbed or digested in the small intestine of man. Oligosaccharides are low in calories and can be used as conventional diet sweeteners such as those used by middle-age and older people who are on special diets due to diabetes.

Oligosaccharides are carbohydrates consisting of 3 to 5 monosaccharides linked together. There are two main methods to produce oligosaccharides. One method involves the application of retrosynthetic reaction of amylase with which the monosaccharides (glucose) are condensed to oligosaccharides. Normally the content of G3 to G5 in the final product is 20%-30% with some other complicated components. G3 and G5 refer to Glucose units. By way of example, G3 refers to a sugar which is comprised of three glucose units linked together as one component.

The other way to make oligosaccharides is the enzymatic hydrolysis method in which the starch is hydrolyzed to polysaccharides first by α-amylases, and then the polysaccharides are further hydrolyzed to oligosaccharides by glucosidase or other enzymes with transglucosylation function. Currently, the enzymatic hydrolysis method is the main process. It is based on starch as raw material. The process comprises two steps. The first step is to get the maltose syrup through starch hydrolysis with α-amylases. The second step is to get the target product through transglucosylation with the co-reaction of two or three kinds of enzymes, and then the routine filtration, decolouration, desalting and concentration processes are applied to get the final product.

Currently, the normal content of oligosaccharides is about 50%-60%. The other main components are glucose and maltose which make about 50% of the final product. The glucose and maltose can disturb the two main health benefits of oligosaccharides product. One is the proliferation of beneficial microbiota Bifidobacteria species in the gastrointestinal tract of humans, and the other is the anti-dental caries benefit. As a result, the health benefits and commercial value of the oligosaccharides product are significantly reduced.

Normally, oligosaccharides with high purity can be obtained by a separation process from the raw oligosaccharides product.

One of separation methods is the membrane separation process. The membrane separation process removes the monosaccharides and disaccharide from the product and keeps the other sugars components with bigger molecular weights, so that the content of oligosaccharides is increased to about 80%. There are problems with this process including the high cost of expensive equipment, low efficiency and difficulties in commercial production.

The other method is the adsorption separation process. The absorption separation process involves removing the monosaccharide and disaccharide by ion exchange columns. The content of oligosaccharides can be increased to 60%-70% by one recycle operation. The disadvantage of this method is that capacity of the columns is low for the single recycle so that multiple recycle adsorption processes are needed to get the high purity oligosaccharides product.

SUMMARY OF THE INVENTION

What is required is a method for the removal of monosaccharide in oligosaccharides production to enhance the health benefits of the resulting product.

According to the present invention there is provided a method for removal of the monosaccharide in oligosaccharides production. The method includes the step of culturing the yeast. A further step involves mixing 8%-12% (W/W) of yeast based on the weight of oligosaccharides and 0.1%-0.5% (W/W) of carbamide as nitrogen source with raw oligosaccharide syrup, and then adjusting the pH value to 4.5-6.0. A further step involves culturing the above oligosaccharides syrup at 23° C.-26° C. for 20-30 hours with intermittent agitation.

The method removes the monosaccharide and disaccharide from raw oligosaccharides by microbial metabolism technology so that the purity and the content of G3 to G5 in oligosaccharides are significantly increased. Oligosaccharides with high purity are thereby obtained at a low cost in terms of equipment and operation. The method can utilize the raw material economically and simplify the commercial process to produce oligosaccharides with high purity.

DETAILED DESCRIPTION OF THE PREFERRED EMBODIMENT

The present invention provides a method for removal of the monosaccharide in oligosaccharides production with selectively microbial metabolism by yeast, with which the purity and the content of G3 to G5 in oligosaccharides is significantly increased. The oligosaccharides with high purity can be obtained at a low cost in terms of equipment and operation. The method economically utilizes the raw material and simplifies the industrial process to produce oligosaccharides with high purity.

The method for removal of the monosaccharide in oligosaccharides production involves the step of activating the yeast with malt extract medium, and then culturing the yeast with glucose growth medium. A further step involves mixing 8%-12% of the yeast (W/W) based on the weight of oligosaccharides and 0.1%-0.5% of carbamide as nitrogen source with raw oligosaccharides liquid, and then adjusting the pH to 4.5-6.0.

Another step involves fermenting the oligosaccharides mixture for 20 to 30 hours at temperature of between 23° C.-26° C. with intermittent agitation.

With the method described above, the yeast is As 2.109 Yeast. The oligosaccharide is the isomaltooligosaccharides with 75% of solid content and the chemical used for pH adjustment is hydrogen chloride.

The method described above, removes the monosaccharide and disaccharide from raw oligosaccharides by microbial metabolism technology so that the purity and the content of G3 to G5 in oligosaccharides are significantly increased. Oligosaccharides with high purity are obtained with low costs in terms of equipment and operation. The technology economically utilizes the raw material and simplifies the process to commercially produce oligosaccharides with high purity.

DESCRIPTION OF EXAMPLES

Application Example 1

Based on the weight of oligosaccharides with content of 75%, As 2.109 yeast was first activated with malt extract medium, and then the yeast was cultured with glucose growth medium. Then 10% ($V_{yeast}/N_{oligosaccharides}$) of the yeast was added to the raw oligosaccharides liquid, followed by 0.2% ($W_{carbmide}/W_{oligosaccharides}$) of carbamide as nitrogen source was mixed with this oligosaccharides liquid. Hydrogen chloride was used to adjust the pH to 5.2. The oligosaccharides mixture was fermented for 22 hours at temperature of 23° C. with intermittent agitation. The samples were analyzed on-line by HPLC to follow the sugar components. The content of glucose GI was 0%, the maltose G2 was 4.2%, and the content of oligosaccharides was 92.56%.

Application Example 2

Based on the weight of oligosaccharides with content of 75%, As 2.109 yeast was first activated with malt extract medium, and then the yeast was cultured with glucose growth medium. Then 11% ($V_{yeast}/N_{oligosaccharides}$) of the yeast was added to the raw oligosaccharides liquid, and followed 0.3% ($W_{carbamide}/W_{oligosaccharides}$) of carbamide as nitrogen source was mixed with this oligosaccharides liquid. Hydrogen chloride was used to adjust the pH to 4.8. The oligosaccharides mixture was fermented for 25 hours at temperature of 25° C. with intermittent agitation. The samples were analyzed on-line by HPLC to follow the sugar components. The content of glucose GI was 0%, the maltose G2 was 5.3%, and the content of oligosaccharides was 94.5%.

Application Example 3

Based on the weight of oligosaccharides with content of 75%, As 2.109 yeast was first activated with malt extract medium, and then the yeast was cultured with glucose growth medium. Then 9.0% ($V_{yeast}/V_{oligosaccharides}$) of the yeast was added into the raw oligosaccharides liquid, and followed by 0.5% ($W_{carbamide}/W_{oligosaccharides}$) of carbamide as nitrogen source was mixed with this oligosaccharides liquid. Hydrogen chloride was used to adjust the pH to 5.8. The oligosaccharides mixture was fermented for 30 hours at temperature of 26° C. with intermittent agitation. The samples were analyzed on-line by HPLC to follow the sugar components. The content of glucose GI was 0%, the maltose G2 was 3.10%, and the content of oligosaccharides was 93.35%.

In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be one and only one of the elements.

It will be apparent to one skilled in the art that modifications may be made to the illustrated embodiment without departing from the spirit and scope of the invention as hereinafter defined in the claims.

The embodiments of the invention in which an exclusive property or privilege is claimed are defined as follows:

1. A method for removal of monosaccharide in an oligosaccharide mixture, the method comprising:
    providing an oligosaccharide mixture containing about 75% non-digestable and non-fermentable isomaltooligosaccharides (W/W), with a balance of the oligosaccharide mixture containing monosaccharides;
    mixing the oligosaccharide mixture with 8%-12% yeast (W/W) based on the weight of the oligosaccharide mixture and 0.1%-0.5% (W/W) of carbamide as a nitrogen source;
    adjusting pH to 4.5-6.0; and
    fermenting the oligosaccharide mixture for 20-30 hours at a temperature of 23° C. to 26° C. while agitating the oligosaccharide mixture intermittently to remove the monosaccharides and increase the percentage of non-digestable and non-fermentable isomaltooligosaccharides in the oligosaccharide mixture.

2. The method according to claim 1 wherein said yeast is As 2.109 Yeast.

3. The method according to claim 1 wherein hydrogen chloride is used to adjust the pH.

4. The method according to claim 1, wherein a resulting content of the non-digestable and non-fermentable isomaltooligosaccharides is about 92.56% to 94.50% (W/W) in the oligosaccharide mixture.

* * * * *